US006960320B1

(12) United States Patent
Smith et al.

(10) Patent No.: US 6,960,320 B1
(45) Date of Patent: Nov. 1, 2005

(54) OIL BURNING LAMPS AND RELATED SYSTEMS

(75) Inventors: Jerald J. Smith, Waukesha, WI (US); David J. Schofield, Milwaukee, WI (US)

(73) Assignee: Lamplight Farms, Inc., Menomonee Falls, WI (US)

( * ) Notice: Subject to any disclaimer, the term of this patent is extended or adjusted under 35 U.S.C. 154(b) by 0 days.

(21) Appl. No.: 10/824,824

(22) Filed: Apr. 15, 2004

(51) Int. Cl.[7] .............................................. A61L 09/00
(52) U.S. Cl. .......................... 422/5; 431/298; 431/320; 431/324; 431/343; 431/362; 422/124; 422/126; 362/171
(58) Field of Search ................ 422/126, 124, 422/5; 431/298, 320, 362, 324, 343; 362/171

(56) References Cited

U.S. PATENT DOCUMENTS

| 651,100 | A |   | 6/1900  | Blakely ...................... 422/126 |
| 1,067,965 | A | * | 7/1913  | Berenger .................... 362/159 |
| 2,774,235 | A | * | 12/1956 | Ruetz ........................ 431/146 |
| 3,355,913 | A | * | 12/1967 | Frangos ...................... 422/125 |
| 4,477,414 | A |   | 10/1984 | Muramoto et al. ......... 422/125 |
| 5,624,230 | A | * | 4/1997  | Taylor et al. .................. 416/5 |
| 5,840,246 | A | * | 11/1998 | Hammons et al. ............. 422/4 |
| 5,840,247 | A |   | 11/1998 | Dubois et al. .............. 422/125 |
| 6,250,912 | B1 |   | 6/2001  | Widdowson ................ 431/324 |
| 6,361,311 | B1 |   | 3/2002  | Smith ......................... 431/291 |
| 6,368,564 | B1 |   | 4/2002  | Smith ......................... 422/123 |
| 6,555,069 | B1 |   | 4/2003  | Ferguson .................... 422/126 |
| 6,562,294 | B1 |   | 5/2003  | Smith ............................. 422/5 |
| 2002/0098128 | A1 |   | 7/2002  | Smith |

FOREIGN PATENT DOCUMENTS

| GB | 1094465 A | 12/1967 | ............ F23D 3/02 |
| JP | 58-158427 | * 9/1983 | ................. 431/144 |
| WO | WO 99/2276 | 10/1998 | ............ A61L 9/03 |

* cited by examiner

*Primary Examiner*—John Kim
*Assistant Examiner*—Brad Y. Chin
(74) *Attorney, Agent, or Firm*—James W. Kayden; Thomas, Kayden, Horstemeyer & Risley, LLP

(57) ABSTRACT

An exemplary oil burning lamp comprises a reservoir configured for storing a supply of oil, a base, a burner tube and a wick. The base is being sized and shaped to receive the reservoir. The burner tube is movably mounted to the reservoir between a retracted position and an extended position. The burner tube has a first end, an opposing second end and at least one opening. In the retracted position, the both ends are located within the reservoir. In the extended position, the first end is located within the reservoir, the second end is located outside the reservoir, and the opening is located such that fragranced components of oil stored in the reservoir can be entrained by air and emanated from the base. The wick is mounted to the burner tube, extends into the reservoir, and extends outwardly from the second end of the burner tube.

15 Claims, 7 Drawing Sheets

OIL BURNING LAMPS AND RELATED SYSTEMS

FIELD OF THE INVENTION

The present invention generally relates to lamps and, more specifically, to oil burning lamps, at least some of which use fragranced oils.

DESCRIPTION OF THE RELATED ART

Oil burning lamps of various types have been used for centuries. Recently, oil burning lamps that include aromatic oils as a source of fuel have become increasingly popular. Of particular interest to consumers is the ability of the lamps to provide both light as well as pleasant fragrances that are produced by fragrance components of the oils.

SUMMARY

Oil burning lamps and related systems are provided. An exemplary embodiment of an oil burning lamp comprises a reservoir, a base, a burner tube and a wick. The reservoir is configured for storing a supply of oil. The base defines an interior and an opening, with the opening communicating with the interior and being sized and shaped to receive the reservoir such that the reservoir can be placed within the interior. The burner tube is movably mounted to the reservoir between a retracted position and an extended position. The burner tube has a first end, an opposing second end and at least one opening formed between the first end and the second end. In the retracted position, the first end and the second end are located within the reservoir. In the extended position, the first end is located within the reservoir, the second end is located outside the reservoir, and the at least one opening is located such that fragranced components of oil stored in the reservoir can be entrained by air and emanated from the base. The wick is mounted to the burner tube. The wick has a first end and a second end, the first end of the wick extending into the reservoir and the second end of the wick extending outwardly from the second end of the burner tube.

An exemplary embodiment of fuel-supply module for an oil burning lamp comprises a reservoir, a wick assembly and a lid. The reservoir defines an interior and an opening, with the opening communicating with the interior and the interior being configured for storing a supply of oil. The wick assembly has a burner tube and a wick. The burner tube is movably mounted to the reservoir between a retracted position and an extended position. The burner tube has a first end and an opposing second end. In the retracted position, the first end and the second end are located within the reservoir. In the extended position, the first end is located within the reservoir and the second end is located outside the reservoir. The wick is mounted to the burner tube and has a first end and a second end. The first end of the wick extends into the reservoir and the second end of the wick extends outwardly from the second end of the burner tube. The lid is sized and shaped for mating with the opening of the reservoir and is movable between a closed position and an open position. In the closed position, the lid seals the oil within the reservoir and retains the burner tube in the retracted position.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

As will be described in detail here, embodiments of an oil burning lamp are presented for providing light and fragrance. Specifically, at least some embodiments of the lamps use fragranced oil as a fuel source that combusts to produce light via a wick assembly. Prior to combustion, at least a portion of the fragrance carrying components of the oil are released by the wick and entrained in a flow of air that emanates from the lamp.

Figure 1:
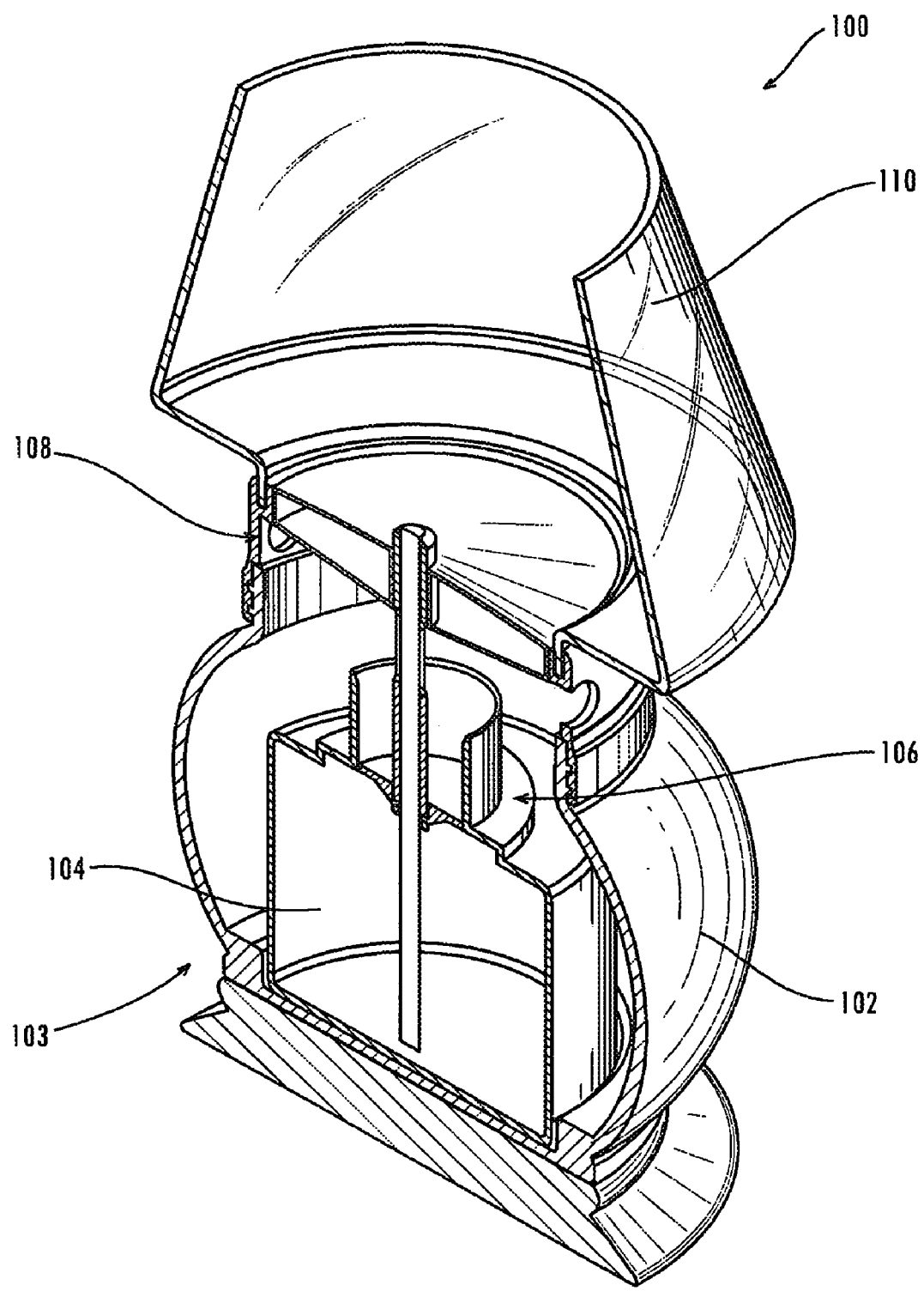
FIG. 1 is a perspective, cut-away view of an embodiment of an oil burning lamp.

Referring now to the drawings, FIG. 1 is a perspective, cut-away view of an embodiment of a lamp 100. Lamp 100 generally incorporates a base 102, a fuel-supply module 103 that includes a reservoir of oil 104 and a wick assembly 106, a fragrance-deflecting assembly 108, and a shade 110.

In operation, oil stored in reservoir 104 is drawn upwardly into the wick assembly 106. Fragrance components of the oil, the evaporation of which is enhanced by the heat of the flame at the distal end of the wick, are directed outwardly from the lamp 100 via fragrance-deflecting assembly 108. The flame also illuminates shade 110, thereby lighting an area within which the lamp is placed. Thus, fragrance and light are provided by lamp 100.

Figure 2:
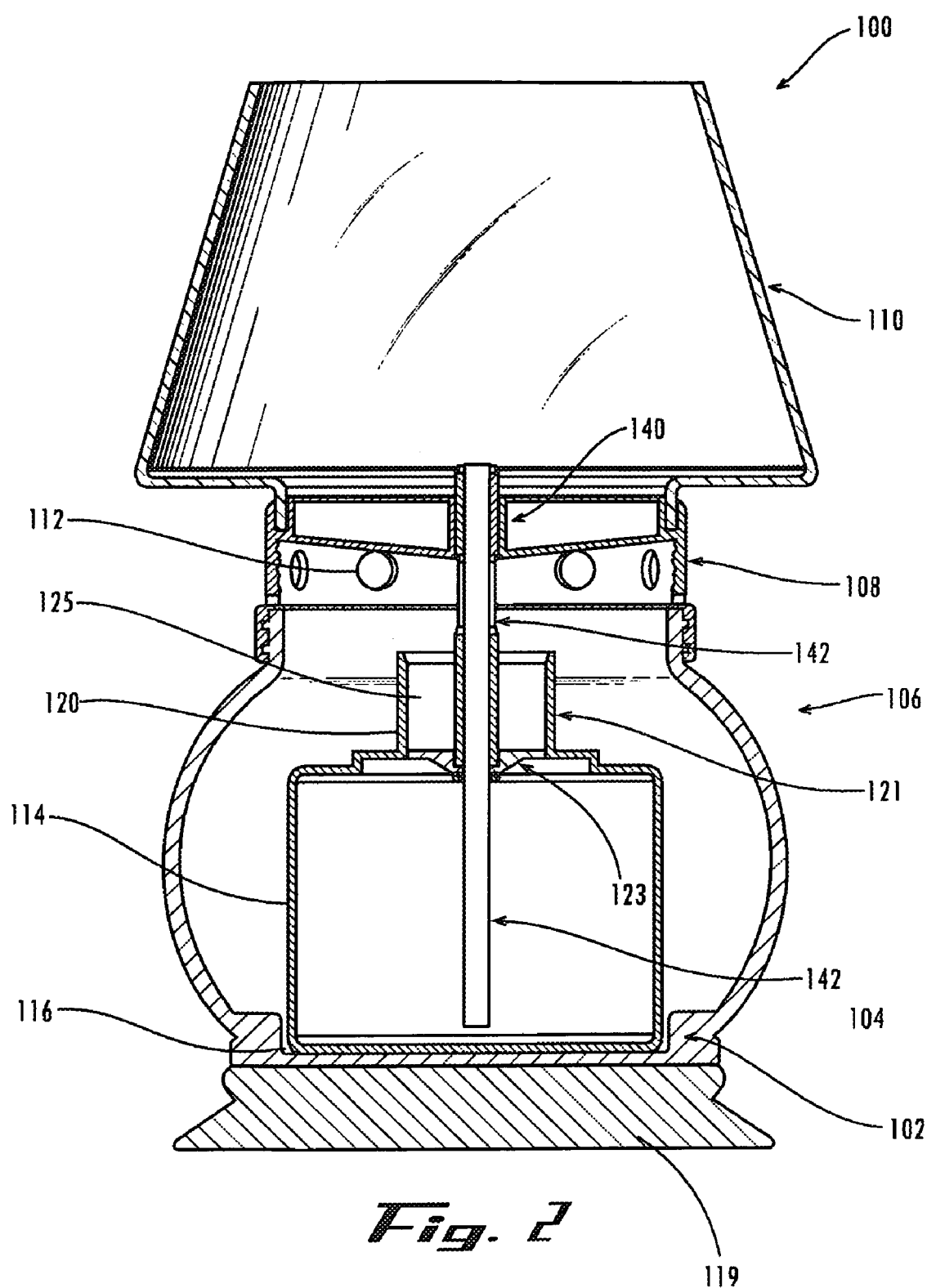
FIG. 2 is a cross-sectional view of the oil burning lamp of FIG. 1.

Turning now to FIG. 2, various components of lamp 100 will be described in greater detail. In FIG. 2, base 102 is a generally spherical structure that has an opening 112 and defines an interior 114. Opening 112 and interior 114 are sized and shaped to accommodate placement of reservoir 104. The interior 114 includes a recess 116 for receiving the bottom 118 of reservoir 104. Note that although embodiment 100 of the lamp is a table top embodiment that incorporates a generally flattened bottom 119 of base 102, other embodiments can be formed in various other configurations. For example, a floor lamp configuration that includes a post can be provided.

Reservoir 104, e.g., a bottle, is generally cylindrical in shape and is configured to retain a supply of oil. Reservoir 104 also has a neck 120 that is sized and shaped to receive an insert 121 of wick assembly 106. Prior to receiving insert 121, opening 122 formed at the distal end of neck 120 typically receives a cap (not shown) so that oil can be securely retained within the reservoir. In some embodiments, the cap can be a child resistant cap that mates with corresponding features formed on the exterior of the neck.

Figure 3:
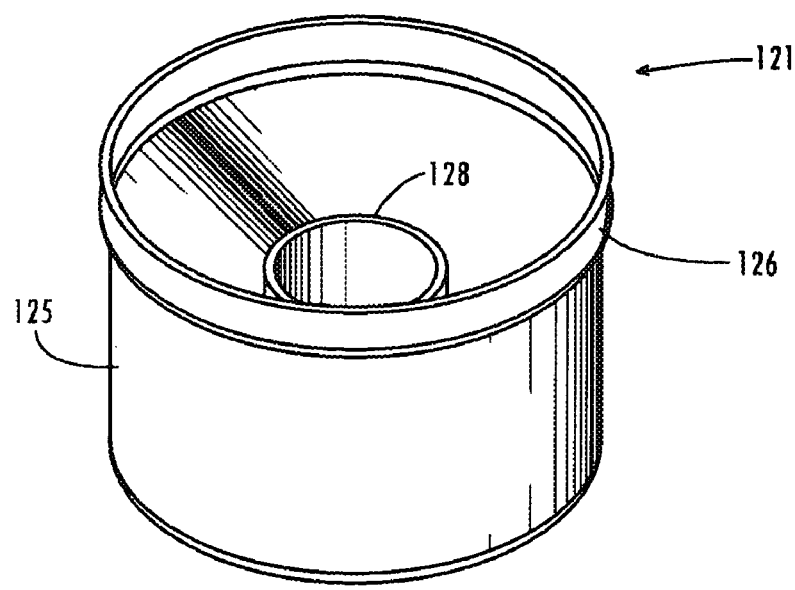
FIG. 3 is a perspective view of an embodiment of an insert.

Wick assembly 106 mates with the reservoir 104, such as by the insert 121 being press fit into the neck 120. With reference to FIG. 3, it is shown that insert 121 is generally cylindrical in shape and includes a base 123 and outer wall 125. An annular flange 126 is located at an upper end of the outer wall. Insert 121 also includes an interior aperture 128 that is aligned with a longitudinal axis of the insert. The annular flange 126 (FIG. 2) serves as a stop that abuts an upper edge 130 of the reservoir. Returning to FIG. 2, the inner aperture 128 receives a burner tube 140 that supports a wick 142, e.g., a cotton braid.

Figure 4:
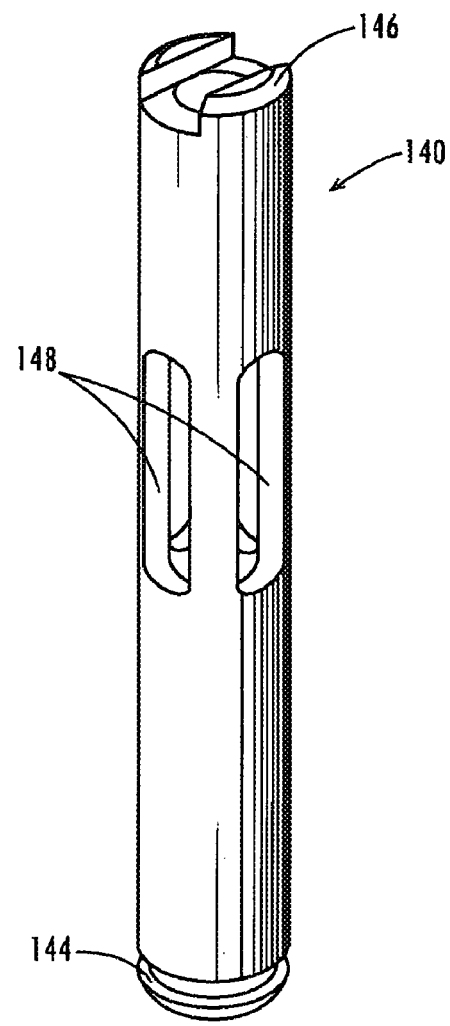
FIG. 4 is a perspective view of an embodiment of a burner tube.

As shown in greater detail in FIG. 4, burner tube 140 is a generally cylindrical structure that includes an annular recess 144 located at its proximal end. A stepped edge 146 is located at the distal end of the burner tube, with longitudinal slots 148 being located at an intermediate portion of the burner tube. Although, the embodiment of FIG. 4 includes four slots, various other numbers and shapes of openings can be used in other embodiments.

Figure 5:
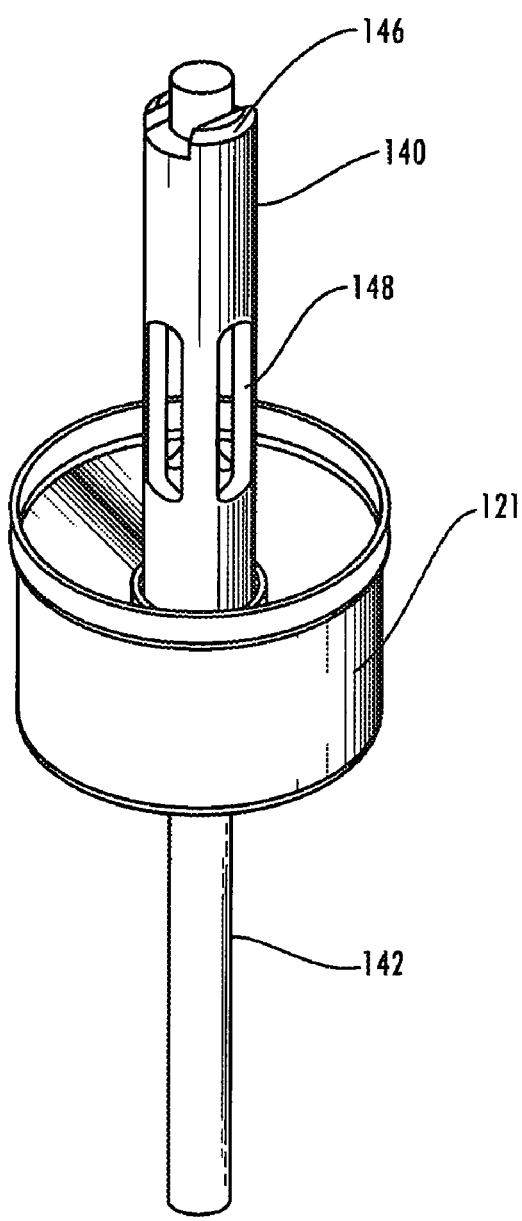
FIG. 5 is a perspective view of an embodiment of a wick assembly.
Figure 6:
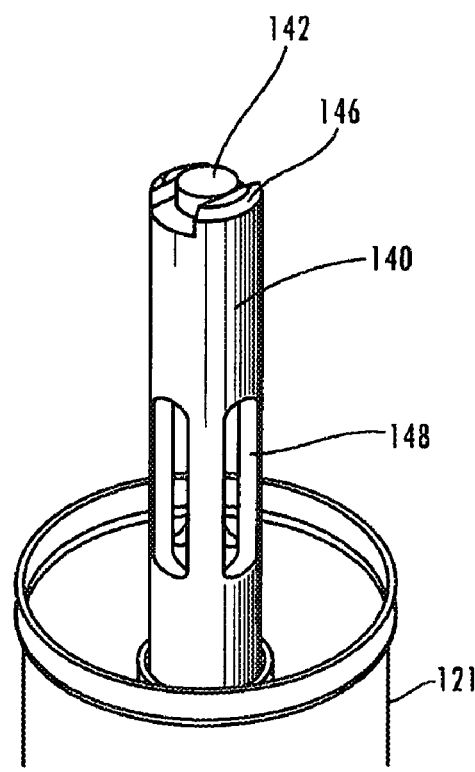
FIG. 6 is a perspective view of the embodiment of FIG. 5, showing detail of the flame-adjustment step.

In FIGS. 5 and 6, a wick 142 is shown inserted into the interior of the burner tube 140 so that at least a portion of the wick extends from the distal end of the burner tube. Although the wick can be extended from the burner tube at various lengths, the stepped edge 146 is formed to a height such that, when the end of the wick is positioned flush with the ends of the stepped edge (FIG. 6), an optimal flame height is selected. By way of example, when a cotton braid wick of an approximate outer diameter of 0.15 inches is used, a step height (and corresponding exposed wick height) of 0.05 to 0.07 inches maintains a flame height at approximately ½ inch. A fixed position of the wick is maintained by piercing the wick with a segment of wire. Although a separate wire can be used in some embodiments, other embodiments use a spring.

As the burner tube 140 typically is formed of metal, heat from a flame formed at the distal end of the wick typically is conducted downwardly toward the insert 121. This heat tends to separate at least some of the fragrance carrying components of the oil that is being wicked from the reservoir 104 from the oil that is to be combusted at the distal end of the wick. These fragrance carrying components can be entrained in air flowing past the slots 148 of the burner tube 140. Thus, heat conducted via the burner tube enhances the aromatic intensity of the fragranced oils emanating from the lamp 100.

Figure 7:
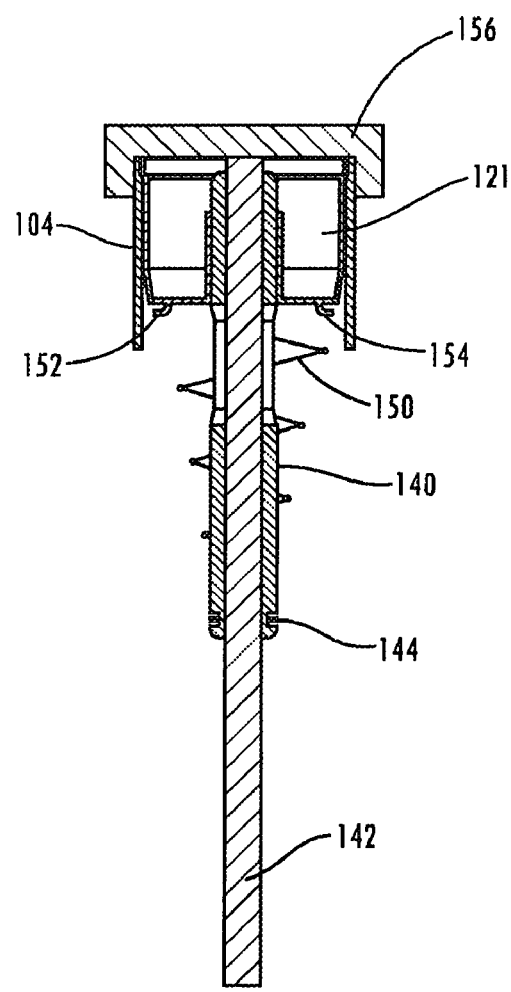
FIG. 7 is a cut-away view of an embodiment of a wick assembly with the burner tube moved to a retracted position.
Figure 8:
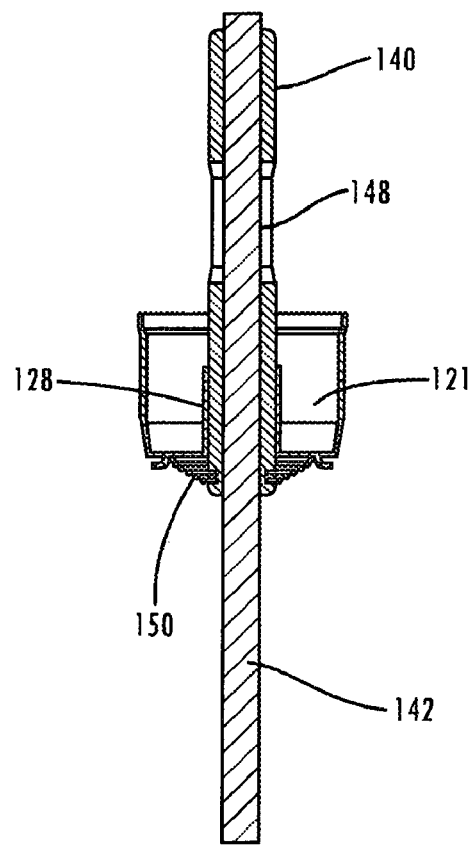
FIG. 8 is a cut-away view of the embodiment of FIG. 7, showing the burner tube in an extended position.

As shown in FIGS. 7 and 8, the burner tube 140 is adjustable with respect to the insert 121 between a retracted position and an extended position. Specifically, FIG. 7 depicts the retracted position, during which the burner tube 140 is moved against spring pressure until the distal end of the burner tube is flush with the annular flange 126 of the insert. In this embodiment, spring pressure is provided by a conical, telescoping spring 150 that is attached to the insert via tabs 152, 154 located at the bottom of the insert, and to the burner tube 140 via the annular recess 144. Placement of the burner tube in the retracted position enables the wick assembly 106 to be stored within the reservoir 104 when a lid 156, e.g., a child-resistant cap, covers the opening of the reservoir. Subsequent removal of the lid enables the spring to urge the burner tube to the extended position for use.

Figure 9:
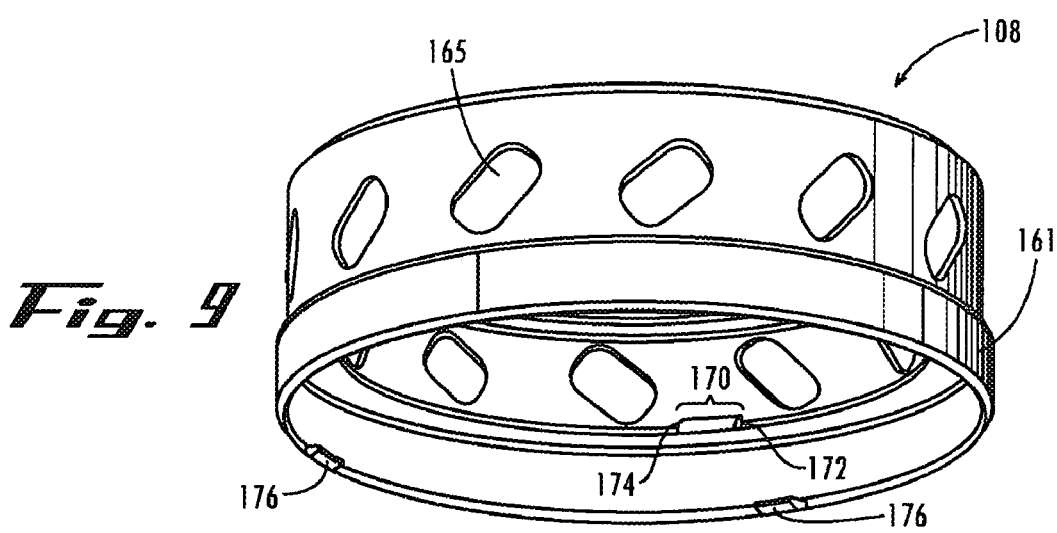
FIG. 9 is a perspective view of an embodiment of a fragrance-deflecting assembly.
Figure 10:
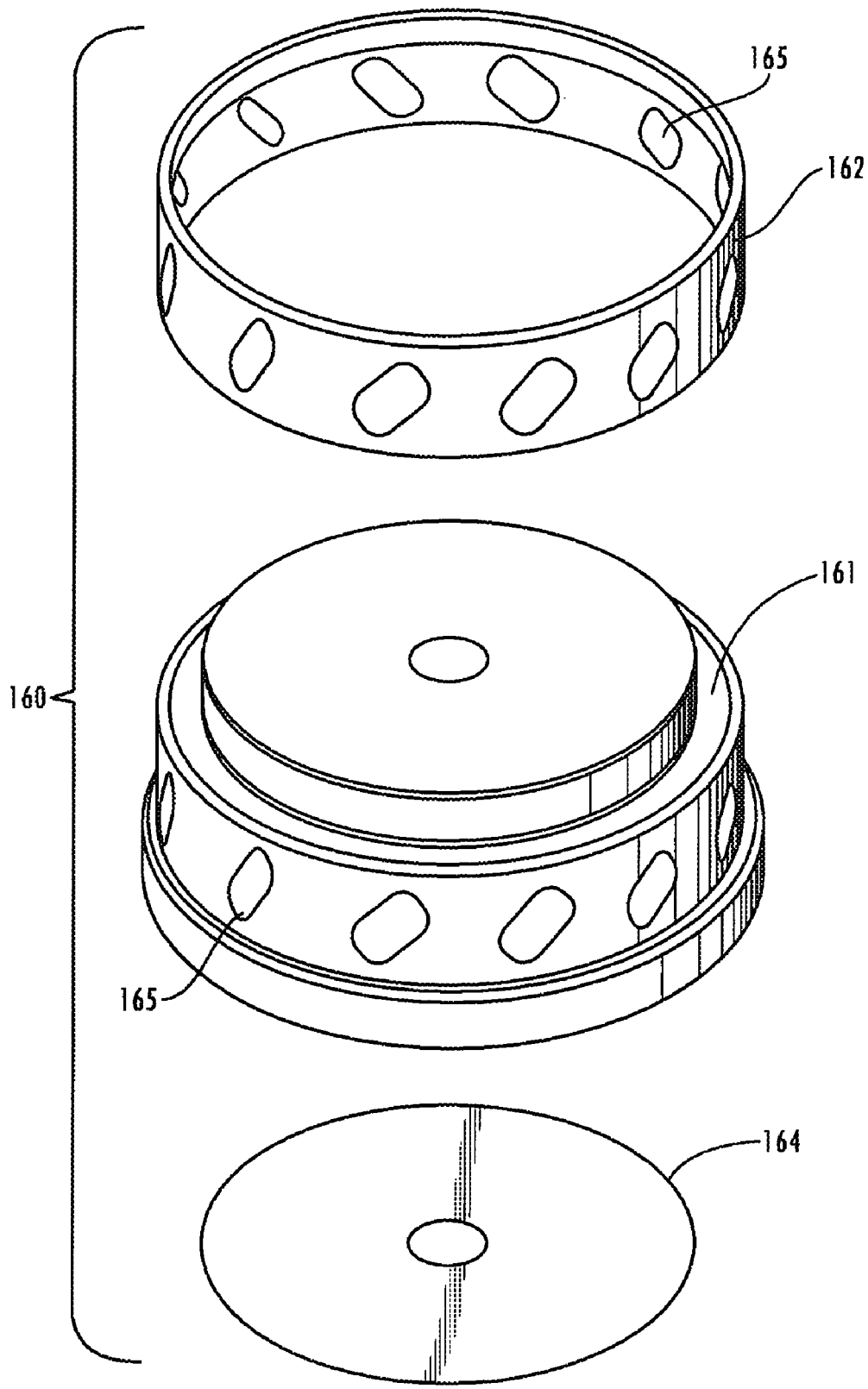
FIG. 10 is a perspective, exploded view of the embodiment of the fragrance-deflecting assembly of FIG. 9.

Referring to FIGS. 9 and 10, an embodiment of a fragrance-deflecting assembly 108 will be described in greater detail. As shown in FIGS. 9 and 10, assembly 108 includes a deflector 164 and an adjustable collar assembly 160, which incorporates a base 161 and a collar 162. Both the base 161 and collar 162 incorporate vent holes 165 that are spaced about the periphery of their respective components so that, when the collar is received about the base, corresponding vent holes can be aligned with each other to permit a fragrance-entrained flow of air to flow through the aligned vent holes. Collar 162 also is movable about the base 161 so that corresponding vent holes can be moved from the aligned positions (previously described) to misaligned positions where a reduced air flow is permitted to flow through the vent holes. That is, when corresponding vent holes are misaligned with each other, the vent hole-containing portions of the collar are aligned with non-vent hole-containing portions of the base, and vice versa.

In the embodiment depicted in FIG. 9, fragrance-deflecting assembly 108 includes a mechanical stop 170 that permits only limited adjustment of the positions of the vent holes of the collar with respect to the base. Specifically, the stop 170 includes a pin 172 attached to the collar that moves within a slot 174 formed in the base. Therefore, movement of the collar is restricted to the distance of travel of the pin within the slot. By way of example, when the pin is at one end of the slot, the vent holes of the collar and base are fully aligned, and when the pin is at the other end of the slot, the vent holes are only slightly aligned.

The deflector 164 is attached to the adjusting collar 160 and is configured to direct the flow of air and entrained fragrance outwardly toward the vent holes of the adjusting collar. Additionally, the deflector can redirect oil condensation back toward the supply of oil, with the condensation typically being collected within the interior of the insert 121.

Figure 11:
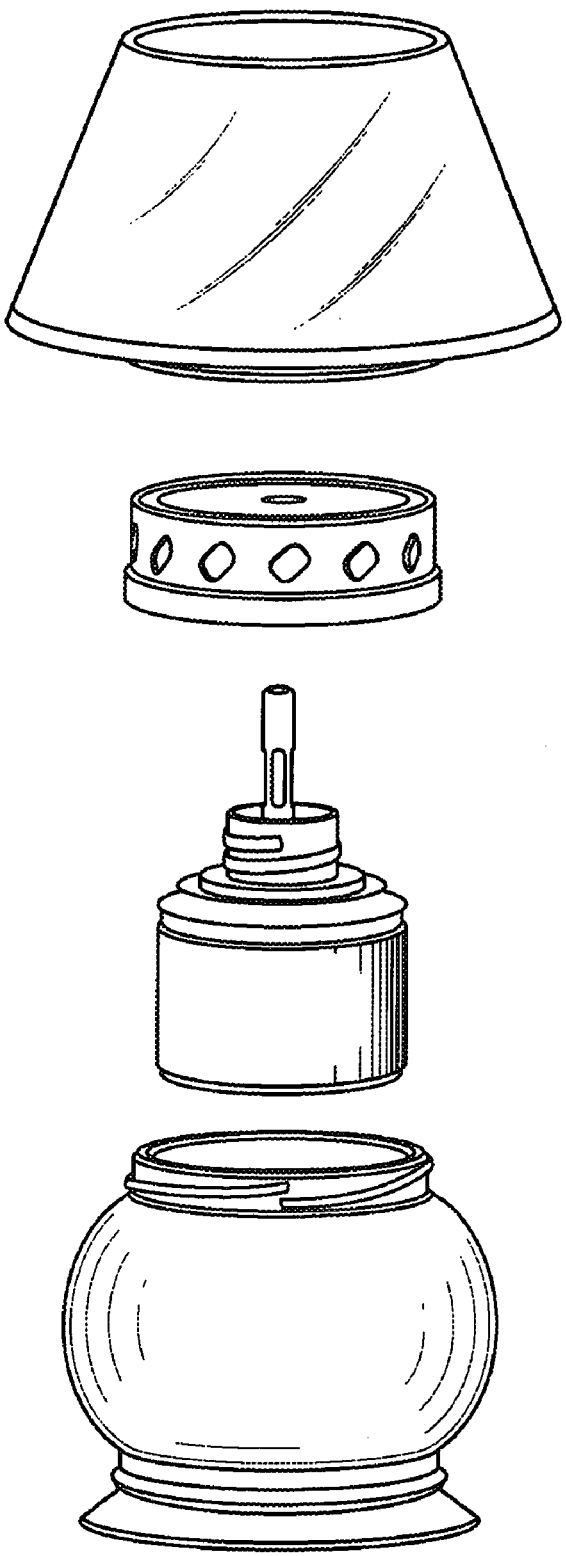
FIG. 11 is a perspective, exploded view of the embodiment of the oil burning lamp.

As shown in FIG. 9, base 161 also includes tabs 176 that extend inwardly from the lower edge of the base. Referring briefly to FIG. 11, these tabs are sized and arranged to engage exterior threads 178 formed at an upper edge of lamp base 102. Thus, engagement of the tabs with the threads and corresponding rotation of the fragrance-deflecting assembly 108 with respect to the lamp base 102 secures the fragrance-deflecting assembly 108 to lamp base 102.

It should be emphasized that many variations and modifications may be made to the above-described embodiments. All such modifications and variations are intended to be included herein within the scope of this disclosure and protected by the following claims.

What is claimed is:

1. An oil burning lamp comprising:
   a reservoir configured for storing a supply of oil;
   a base defining an interior and an opening, the opening communicating with the interior and being sized and shaped to receive the reservoir such that the reservoir can be placed within the interior;
   a burner tube movably mounted to the reservoir between a retracted position and an extended position, the burner tube having a first end, an opposing second end and at least one opening formed between the first end and the second end, in the retracted position the first end and the second end being located within the reservoir, in the extended position the first end being located within the reservoir, the second end being located outside the reservoir, the at least one opening being located such that fragranced components of oil stored in the reservoir can be entrained by air and emanated from the base;

a wick mounted to the burner tube, the wick having a first end and a second end, the first end of the wick extending into the reservoir and the second end of the wick extending outwardly from the second end of the burner tube.

2. The lamp of claim 1, wherein the second end of the burner tube has a stepped ledge, a height of the stepped ledge being selected to correspond to a flame height of a flame formed at the second end of the wick.

3. The lamp of claim 1, further comprising:

an insert having an outer wall and an inner aperture, the inner aperture being sized and shaped to receive the burner tube, the outer wall being sized and shaped to be received by the reservoir.

4. The lamp of claim 3, further comprising:

a spring attached between the burner tube and the insert and biased to retain the burner tube in the extended position.

5. The lamp of claim 4, wherein the insert has tabs located on a bottom thereof, the tabs securing the spring to the insert.

6. The lamp of claim 4, wherein the burner tube has an annular recess and the spring is secured to the burner tube via the annular recess.

7. The lamp of claim 1, further comprising:

oil located in the reservoir.

8. The lamp of claim 7, wherein the oil is fragranced oil.

9. The lamp of claim 4, wherein the base has recess located within the interior and the reservoir seats within the recess.

10. The lamp of claim 1, further comprising:

a fragrance-deflecting assembly positioned such that at least a portion of the fragrance-deflecting assembly is between the base and the second end of the burner tube, the fragrance-deflecting assembly being operative to direct a flow of air outwardly from the burner tube.

11. The lamp of claim 10, wherein the fragrance-deflecting assembly has a base and a collar, the base and the collar having corresponding vent holes, the collar being movable with respect to the base such that the corresponding vent holes are alignable by moving the collar with respect to the base for controlling the flow of air.

12. The lamp of claim 1, further comprising:

means for directing a flow of air outwardly from the burner tube.

13. A fuel-supply module for an oil burning lamp, said fuel supply module comprising:

a reservoir defining an interior and an opening, the opening communicating with the interior, the interior being configured for storing a supply of oil a wick assembly having a burner tube and a wick, the burner tube being movably mounted to the reservoir between a retracted position and an extended position, the burner tube having a first end and an opposing second end, in the retracted position the first end and the second end being located within the reservoir, in the extended position the first end being located within the reservoir, the second end being located outside the reservoir, the wick mounted to the burner tube, the wick having a first end and a second end, the first end of the wick extending into the reservoir and the second end of the wick extending outwardly from the second end of the burner tube; and a lid sized and shaped for mating with the opening of the reservoir and movable between a closed position and an open position, in the closed position the lid sealing the oil within the reservoir and retaining the burner tube in the retracted position.

14. The fuel-supply module of claim 13, wherein the lid is a child resistant cap.

15. The fuel-supply module of claim 13, wherein the burner tube has at least one opening formed between the first end and the second end.

* * * * *